United States Patent [19]
Sato et al.

[11] Patent Number: 5,574,185
[45] Date of Patent: Nov. 12, 1996

[54] PRODUCTION OF N-(α-ALKOXYETHYL) FORMAMIDE

[75] Inventors: Shin-ichi Sato; Kiyoji Kuma, both of Kitakyusyu, Japan

[73] Assignee: Mitsubishi Chemical Corporation, Tokyo, Japan

[21] Appl. No.: 346,605

[22] Filed: Nov. 16, 1994

[51] Int. Cl.⁶ .................................................. C07C 233/05
[52] U.S. Cl. ............................................ 564/224; 564/215
[58] Field of Search ....................................... 564/215, 224

[56] References Cited

U.S. PATENT DOCUMENTS 4,567,300  1/1986  Murao et al. ............................ 564/215
4,670,591  6/1987  Oftring et al. .......................... 564/224

FOREIGN PATENT DOCUMENTS

0251118B1  1/1990  European Pat. Off. .
1286356   12/1986  Japan ....................................  564/224

Primary Examiner—Shailendra Kumar
Attorney, Agent, or Firm—David G. Conlin; Peter F. Corless

[57] ABSTRACT

An improved process for producing N-(α-alkoxyethyl)formamide by reacting formamide with acetaldehyde in the presence of a basic catalyst, thereby giving N-(α-hydroxyethyl)formamide, and reacting it with a primary or secondary alcohol in the presence of an acid catalyst, thereby giving N-(α-alkoxyethyl)formamide, characterized in that the basic catalyst is alkali metal bicarbonate or alkali metal hydrogenphosphate.

11 Claims, No Drawings

PRODUCTION OF N-(α-ALKOXYETHYL) FORMAMIDE

BACKGROUND OF THE INVENTION

1. Field of the Invention

The present invention relates to a process for producing stabilized N-(α-alkoxyethyl)formamide. This compound is useful as an intermediate for the synthesis of N-vinylformamide.

2. Description of the Prior Art

A process for producing N-(α-alkoxyethyl)formamide is disclosed in U.S. Pat. No. 4,567,300. It consists of reacting formamide with acetaldehyde in the presence of a basic catalyst to give N-(α-hydroxyethyl) formamide and alkoxylating it subsequently. According to the disclosure, the basic catalyst should preferably be a weakly basic one which is composed of a strong base (such as hydroxide of lithium, sodium, or potassium) and a weak acid ( such as organic acid, phenol, sulfurous acid, phosphorous acid, carbonic acid, and phosphoric acid) which has a $pK_a$ value of 4–15. Sodium carbonate is used as the basic catalyst in Example.

The above-mentioned process proceeds rather stoichiometrically, but the actual yield is low after purification that follows alkoxylation. In fact, the reaction product is freed of excess alcohol and water formed by the reaction and finally distilled. The low yield is due to the fact that N-(α-alkoxyethyl)formamide is so poor in thermal stability that it decomposes during distillation.

In view of the foregoing, the present inventors extensively studied the production and thermal stability of N-(α-alkoxyethyl)formamide. As the result, we unexpectedly found that it is possible to produce thermally stable N-(α-alkoxyethyl)formamide in high yields by using a specific basic catalyst. This finding led to the present invention.

SUMMARY OF THE INVENTION

The gist of the present invention resides in an improved process for producing N-(α-alkoxyethyl)formamide by reacting formamide with acetaldehyde in the presence of a basic catalyst, thereby giving N-(α-hydroxyethyl)formamide, and reacting it with a primary or secondary alcohol in the presence of an acid catalyst, thereby giving N-(α-alkoxyethyl)formamide, characterized in that the basic catalyst is alkali metal bicarbonate or alkali metal hydrogenphosphate.

DETAILED DESCRIPTION OF THE INVENTION

A detailed description of the invention follows. The process of the present invention employs formamide and acetaldehyde as the starting materials. They may be of commercial grade; however, they should preferably be purified by distillation so as to reduce the content of diformamide in formamide below 1000 ppm (by weight) and the content of acetic acid in acetaldehyde below 300 ppm (by weight).

The present invention is characterized by that the reaction of formamide with acetaldehyde needs a basic catalyst which is alkali metal bicarbonate or alkali metal hydrogenphosphate, the former including potassium bicarbonate, sodium bicarbonate, and lithium bicarbonate, and the latter including potassium hydrogenphosphate, sodium hydrogenphosphate, and lithium hydrogenphosphate.

The catalyst should be used in an amount of 0.01–10 mol %, preferably 0.2–5 mol %, of formamide. Formamide and acetaldehyde as the starting materials should be used in a molar ratio of from 1:1 to 1:5, preferably 1:1.0 to 1:1.5. The reaction temperature should be 10°–100° C., preferably 10°–40° C.

The reaction may be carried out in the absence of solvent; however, a solvent is usable particularly in the case where the reaction temperature is lower than the melting point (52.5°–53.8° C.) of N-(α-hydroxyethyl)formamide. Examples of the solvent include aliphatic hydrocarbons (such as hexane and heptane) and aromatic hydrocarbons (such as benzene, toluene, and xylene) which do not substantially dissolve the reaction product. The amount of solvent should be such that the reaction product is completely dispersed. It is 0.2–2 times (by weight) as much as formamide. I addition, the solvent may be added into the reaction system when the reaction proceeding.

The reaction product (N-(α-hydroxyethyl)formamide) eventually crystallizes out of the reaction system; however, it is desirable to cool the reaction system or to add seed crystals to the reaction system to promote crystallization and increase yields when the conversion of formamide has reached 50–80%, preferably 60–80%. The cooling temperature ranges from –20° C. to 30° C., preferably from 0° C. to 20° C. The addition of seed crystals may be accomplished in the usual way.

Crystallized N-(α-hydroxyethyl)formamide may be readily recovered from the reaction system by filtration. If crystallization does not take place or it is not necessary to recover crystals, it is possible to add an alcohol to the reaction liquid for alkoxylation.

The thus obtained N-(α-hydroxyethyl)formamide is subsequently reacted with an alcohol to give N-(α-alkoxyethyl)formamide. The alcohol is a primary or secondary alcohol which has 1–8, preferably 1–4, carbon atoms. It includes, for example, methanol, ethanol, n-propanol, n-butanol, and isobutyl alcohol.

The alcohol as a reactant may also perform an additional function, which permits the alcohol to be used in greatly varied amounts. If the alcohol is intended to facilitate the recovery of the reaction product, its amount should be 1 to 30 times as much as N-(α-hydroxyethyl)formamide (in molar ratio). If the alcohol is intended for use also as a solvent, its amount should be 2 to 20 times as much as N-(α-hydroxyethyl)formamide (in molar ratio). The amount of the alcohol may be reduced to 1–5 times as much as N-(α-hydroxyethyl)formamide (in molar ratio) by adding an inert solvent in proper amount.

The reaction is catalyzed by an acid catalyst, which includes mineral acid, organic acid, ion exchange resin with weak or strong acidity, and solid acid. Preferred examples of the acid catalysts are strong acids, such as sulfuric acid, hydrochloric acid, nitric acid, hydrobromic acid, sulfamic acid, sulfamic acid, methanesulfonic acid, ethanesulfonic acid, paratoluenesulfonic acid, and cross-linked polystyrenesulfonic acid. The acid catalyst should be used in an amount of 0.001–10 mol %, preferably 0.1–5 mol %, of N-(α-hydroxyethyl)formamide.

The reaction of N-(α-hydroxyethyl)formamide with an alcohol may be accomplished by adding an acid catalyst to the mixture of the reactants, or by mixing a solution of an acid catalyst in an alcohol with N-(α-hydroxyethyl)formamide. The reaction temperature ranges from –10° C. to 60° C., preferably from 0° C. to 40° C., for the desired reactivity and stability of N-(α-hydroxyethyl)formamide.

When the reaction is complete, the acid catalyst is neutralized with sodium hydroxide, potassium hydroxide, or ammonia water, or removed, and the reaction product is freed of low-boiling fractions (such as alcohol and water) by concentration. The desired N-(α-alkoxyethyl)formamide is isolated and purified by distillation under reduced pressure using a packed column having a theoretical plate number of 2–30, with the pressure and temperature at the top of the column being 2–30 mmHg and 70°–100° C., respectively.

The thus obtained N-(α-methoxyethyl)formamide was heated in nitrogen at 120° C. for 1 hour to test its thermal stability. The results are shown in Table 1.

EXAMPLES 2 TO 6 AND COMPARATIVE EXAMPLE 1 TO 6

The same procedure as in Example 1 was repeated except that the kind and amount of the basic catalyst were changed as shown in Table 1. The results are shown in Table 1.

TABLE 1

| Example No. | Basic catalyst Name | Amount (mol %)* | Yield of N-(α-hydroxyethyl)formamide (%)* | Yield of N-(α-methoxyethyl)fomamide (%)* | Ratio of decomposition of N-(α-methoxyethyl)fomamide (%) |
|---|---|---|---|---|---|
| Example 1 | Potassium bicarbonate | 0.30 | 98.3 | 95.4 | 2.9 |
| Example 2 | Potassium bicarbonate | 0.60 | 99.4 | 96.4 | 3.0 |
| Example 3 | Potassium bicarbonate | 1.00 | 99.4 | 96.4 | 3.1 |
| Example 4 | Potassium hydrogenphosphate | 0.30 | 98.1 | 95.2 | 2.8 |
| Example 5 | Potassium hydrogenphosphate | 0.60 | 99.3 | 96.3 | 3.0 |
| Example 6 | Potassium hydrogenphosphate | 1.00 | 99.3 | 96.3 | 3.0 |
| Comparative Example 1 | Potassium carbonate | 0.10 | 90.5 | 87.8 | 10.0 |
| Comparative Example 2 | Potassium carbonate | 0.15 | 99.2 | 96.2 | 12.0 |
| Comparative Example 3 | Potassium carbonate | 0.30 | 99.3 | 96.3 | 15.0 |
| Comparative Example 4 | Potassium phosphate | 0.10 | 83.2 | 75.0 | 18.5 |
| Comparative Example 5 | Potassium phosphate | 0.30 | 98.2 | 95.4 | 20.2 |

*based on the amount of formamide

To further illustrate the invention, and not by way of limitation, the following examples are given.

EXAMPLE 1

A 2-liter glass reactor, equipped with a stirrer and thermostat, was charged with 800 g of toluene. Air in the reactor was displaced by nitrogen. The reactor was charged with 235 g of acetaldehyde, with its temperature adjusted to 20° C. The reactor was charged over 30 minutes with 20% of a solution of 1.33 g of potassium bicarbonate in 200 g of formamide. (1.33 g is equivalent to 0.3 mol % of formamide.) After ageing for 30 minutes, the reactor was charged with 0.5 g of N-(α-hydroxyethyl)formamide as seed crystals for crystallization of N-(α-hydroxyethyl)formamide. Ageing was continued for another 30 minutes. The remainder of the formamide solution was added over 2.5 hours, and the reaction product was allowed to stand for ageing for 1 hour. The reaction product (in the form of slurry) was separated from toluene, and the amount of N-(α-hydroxyethyl)formamide obtained was determined by liquid chromatography. The results are shown in Table 1.

The N-(α-hydroxyethyl)formamide was etherified with 430 g of methanol containing 3.5 of sulfuric acid by stirring at 20° C. for 1 hour. The reaction product was neutralized with 25% sodium hydroxide, and the salt which had separated out was filtered out. Low-boiling fractions (composed mainly of methanol) were removed by vacuum distillation (at 50 mmHg) using a rotary evaporator (at a bath temperature of 60° C.). Thus there was obtained N-(α-methoxyethyl)formamide in a yield shown in Table 1.

EFFECT OF THE INVENTION

The process of the present invention permits the production of thermally stable N-(α-alkoxyethyl)formamide from formamide, acetaldehyde, and alcohol. Therefore, it greatly contributes to the industrial production of N-vinylformamide.

What is claimed is:

1. A process for producing N-(α-alkoxyethyl)formamide comprising reacting formamide with acetaldehyde in the presence of a basic catalyst selected from the group consisting of potassium bicarbonate and potassium hydrogenphosphate, thereby giving N-(α-hydroxyethyl)formamide, and reacting the N-(α-hydroxyethyl)formamide with a primary or secondary alcohol in the presence of an acid catalyst, thereby giving N-(α-alkoxyethyl)formamide.

2. A process as defined in claim 1, wherein the formamide is one which contains diformamide in an amount less than 1000 ppm (by weight).

3. A process as defined in claim 1, wherein the acetaldehyde is one which contains acetic acid in an amount less than 300 ppm (by weight).

4. A process as defined in claim 1, wherein the basic catalyst is used in an amount of 0.01–10 mol % of the formamide.

5. A process as defined in claim 1, wherein the formamide and acetaldehyde are used in a molar ratio of from 1:1.0 to 1:5.0.

6. A process as defined in claim 1, wherein the reaction is carried out in a solvent selected from aliphatic hydrocarbons and/or aromatic hydrocarbons.

7. A process as defined in claim 1, wherein the primary or secondary alcohol is an alcohol having 1–8 carbon atoms.

8. A process as defined in claim 1, wherein the acid catalyst is used in an amount of 0.001–10 mol % of N-(α-hydroxyethyl)formamide.

9. A process for purifying the N-(α-alkoxyethyl)formamide produced according to claim 1, said process comprising vacuum distillation by a column.

10. The process of claim 1 wherein the basic catalyst is potassium bicarbonate.

11. The process of claim 1 wherein the basic catalyst is potassium hydrogenphosphate.

* * * * *